United States Patent

Svara

Patent Number: 5,214,179
Date of Patent: May 25, 1993

[54] CYCLIC ACYLPHOSPHINIC ACID DERIVATIVES AND PROCESS FOR THEIR PREPARATION

[75] Inventor: Jürgen Svara, Cologne, Fed. Rep. of Germany

[73] Assignee: Hoechst Aktiengesellschaft, Frankfurt am Main, Fed. Rep. of Germany

[21] Appl. No.: 878,664

[22] Filed: May 4, 1992

[30] Foreign Application Priority Data

May 16, 1991 [DE] Fed. Rep. of Germany ....... 4115946

[51] Int. Cl.⁵ .......................................... C07F 9/6574
[52] U.S. Cl. ...................................... 558/83; 558/95; 558/96
[58] Field of Search ............................ 558/83, 96, 95

Primary Examiner—Joseph Paul Brust
Assistant Examiner—Michael G. Ambrose
Attorney, Agent, or Firm—Connolly & Hutz

[57] ABSTRACT

The invention relates to cyclic acylphosphinic acid derivatives of the formula

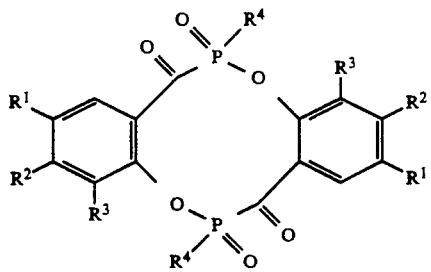

in which the substituents independently of each other can have the following meaning:

$R^1$, $R^2$, $R^3$=H, halogen C1- to C10-alkyl or -alkoxy phenyl, phenoxy, acetyl or $NO_2$, where $R^1$ and $R^2$ together, with incorporation of the associated aromatic 6-ring, can also form an extended, unsubstituted or substituted aromatic ring system;

$R^4$=C1- to C4-alkyl, C5- or C6-cycloalkyl, phenyl or alkylphenyl.

The novel cyclic acylphosphinic acid derivatives can be prepared by reacting aromatic o-hydroxycarboxylic acids with organyldichlorophosphines of the formula $R^4OCl_2$ in an aprotic solvent or suspension medium at 0° to 200° C. with elimination of HCl and separating off, washing and drying the precipitated target product.

4 Claims, No Drawings

CYCLIC ACYLPHOSPHINIC ACID DERIVATIVES AND PROCESS FOR THEIR PREPARATION

The invention relates to novel cyclic acylphosphinic acid derivatives of the formula

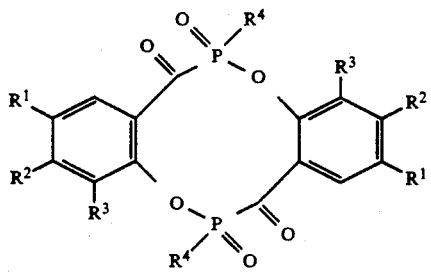

in which the substituents independently of each other can have the following meaning: $R^1$, $R^2$, $R^3$=H, halogen, C1- to C10-alkyl or -alkoxy, phenyl, phenoxy, acetyl or $NO_2$, where $R^1$ and $R^2$ together, with incorporation of the associated aromatic 6-ring, can also form an extended, unsubstituted or substituted aromatic ring system;

$R^4$=C1- to C4-alkyl, C5- or C6-cycloalkyl, phenyl or alkylphenyl.

The substituents $R^1$ and $R^2$ can together form for example a benzo group, i.e. the aromatic benzene unit present can be extended to give an aromatic naphthalene unit. The methoxyl group, for example, can act as a possible substituent in this extended aromatic ring system (cf. Example 16).

Preference is given to cyclic acylphosphinic acid derivatives of the abovementioned formula, in which the substituents independently of each other can have the following meaning:

$R^1$, $R^2$, $R^3$=H, Cl, Br, $CH_3$, $CH_3O$, $CH_3HO$ or $NO_2$, where $R^1$ and $R^2$ together, with incorporation of the associated aromatic 6-ring, can also form a naphthalene structure, optionally substituted by a methoxyl group;

$R^4$=methyl, sec-butyl or phenyl.

The novel cyclic acylphosphinic acid derivatives can be used as photoinitiators.

The invention further relates to a process for the preparation of the abovementioned novel cyclic acylphosphinic acid derivatives, wherein aromatic o-hydroxy-carboxylic acids of the formula

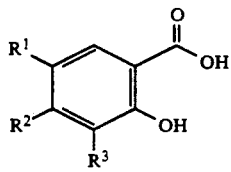

or their alkali metal salts are reacted with organyldiphines of the formula $R^4PCl_2$, where $R^1$, $R^2$ and $R^3$ and $R^4$ have the meaning given, in an aprotic solvent or suspension medium at temperatures of 0° to 200° C., preferably 20° to 150° C., with elimination of gaseous hydrogen chloride or precipitation of alkali metal chloride and the precipitated target product is separated off, washed and dried.

Aprotic solvents or suspension media are those which are inert to a P-Cl group and HCl, for example toluene, xylene, halogenated hydrocarbons, petroleum ether, alkanes, ethers (methyl tert-butyl ether, diisopropyl ether, glycol ether) or ether esters of glycol (for example methyl glycol acetate). The aprotic solvents or suspension media to be used must, of course, have a boiling point which is above the selected reaction temperature or which exactly corresponds to it.

The alkali metal salts of the aromatic o-hydroxycarboxylic acid derivatives to be used are preferably the sodium and potassium salts.

The starting materials are generally used in stoichiometric weight ratios, i.e. in identical molar amounts (1:1), although molar ratios of 1:2 to 2:1 are possible.

In view of the reaction temperature, a procedure employing reflux of the solvent or suspension medium is preferred.

The reaction according to the invention can be carried out in the presence of catalytic amounts of heterocyclic, aromatic compounds or quaternary ammonium salts or phosphonium salts, which accelerate the reaction of P-Cl groups with OH groups. For example, pyridines, preferably dimethylaminopyridines, quinolines or imidazoles are suitable catalysts. When a catalyst is used, this can be added in amounts of 0.1 to 10 mol %, based on the aromatic o-hydroxycarboxylic acid used. In contrast thereto, the addition of an acid binder, for example a tertiary amine, in a roughly stoichiometric molar ratio to trap the hydrogen chloride in the reaction mixture is not advantageous, since in this case, as expected, compounds having a 6-ring structure of the type

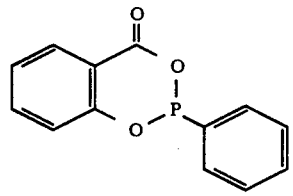

form.

The reaction temperature is generally selected depending on the reactivity of the starting materials. The length of reaction is of secondary importance and is generally shorter when the reaction temperature is high. The length of reaction can be between 1 and 75 hours.

The work-up of the target products is carried out by standard methods of preparative organic chemistry. The target products are frequently crystalline and are isolated by filtration, if required, after concentration or cooling of the reaction mixture.

When alkali salts of the aromatic o-hydroxycarboxylic acids are used, the resulting alkali metal chloride must either be removed by filtration or by washing the reaction mixture or the separated crude product using water.

Example (1) Reaction of salicylic acid with phenyldichlorophosphine $PhPCl_2$

Phenyldichlorophosphine (37.1 g; 208 mmol) is added dropwise to a suspension of salicyclic acid (28.7 g; 208 mmol) in xylene (100 ml). On heating, HCl formation occurs and the solution turns yellow. The salicyclic acid slowly dissolves with steady gas formation. The reaction mixture is stirred for 72 h at 75° C., a crystalline solid precipitating out. After cooling, the precipitated solid is filtered off using suction, washed using toluene and dried in vacuo. A fine crystalline, colorless powder is obtained.

Formula:

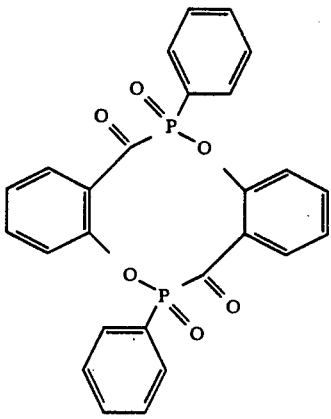

Name: 7,14-dioxo-6,13-diphenyl-dibenzo[d,i]-1,6-dioxa-2,7-diphosphecane 6,13-dioxide
Yield: 31.5 g (62.3% of theory)
NMR-data: $^{31}$P (CDCl$_3$): 31.0 ppm; $^1$H (80 MHz, CCl$_3$): 6.8–8.0 ppm (multiplet) $^{13}$C (100 MHz, CDCl$_3$): 146.8 ppm; multiplet; C=O 135.8 ppm; multiplet; C-O 133.6 ppm; singlet; C-H (benzo-);
131.7 ppm; multiplet; C-H (P-phenyl);
131.3 ppm; singlet; C-H (benzo-);
128.4 ppm; multiplet; C-H (P-phenyl);
128.0 ppm; singlet; C-H (P-phenyl);
125.8 ppm; singlet; C-H (benzo-);
124.3 ppm; doublet; $^1$J(C-P)=188.2Hz; (P-phenyl);
123.8 ppm; singlet (broad); C-CO;
121.6 ppm; singlet; CH-C-O;
MS (direct injection, 70 eV): m/e (I$_{rel}$, fragment): 488 (100, M+); 348 (16, M-PhPO$_2$+); high resolution found (calculated): 488.0578 (488.057866)
UV (acetonitrile: Maximum at 283 nm.

Example (2) Reaction of salicylic acid with phenyldichlorophosphine PhPCl$_2$ As in Example 1, salicylic acid (600 q; 4.4 mol) in methyl glycol acetate (1100 ml) is reacted with PhPCl$_2$ (778 g; 4.4 mol) for 5 h at 140° C. After cooling and work-up, a colorless to pale yellow, crystalline solid is obtained.
Yield: 456 g (41.1 % of theory)
$^{31}$O-NMR (CDCl$_3$): 30.5 ppm.

Example (3) Reaction of salicylic acid with phenyldichlorophosphine PhPCl$_2$ Analogously to Example 1, salicylic acid (69 g; 0.5 mol) is brought to reaction with PhPCl$_2$ (89.5 g; 0.5 mol) for 24 h at 115° C. in toluene.
Yield: 40 g (32.5 % of theory)
$^{31}$P-NMR (CDCl$_2$): 30.9 ppm.

Example (4) Reaction of sodium salicylate with phenyldi chlorophosphine PhPCl$_2$ Sodium salicylate (84.7 g, 529 mmol) is reacted in toluene (120 ml) with PhPCl$_2$ (94.7 g, 529 mmol) (temperature: 110° C.; reaction time: 7 h). The precipitated solid is separated off, slurried using water and filtered off once more. After further washing with water to remove NaCl and drying, a crystalline, still somewhat impure product is obtained.
Yield: 82.7 g (64% of theory); after recrystallization from anhydrous acetic acid: 45 g (34.8% of theory)
$^{31}$P-NMR (CDCl$_2$) 31.0 ppm.

Example (5) Reaction of salicylic acid with methyldichlorophosphine

Methyldichlorophosphine (68 g; 0.58 mol) is added dropwise to a suspension of salicylic acid (80 g; 0.58 mol) in toluene (100 ml) at 100° C. Vigorous HCl formation occurs immediately and the solution turns yellow. The salicylic acid dissolves wi&h simultaneous gas formation. The reaction mixture is stirred for 4 h at 110° C., a crystalline solid being precipitated. After cooling, the precipitated solid is filtered off using suction, washed using toluene and dried. A fine crystalline, colorless powder is obtained.

Formula:

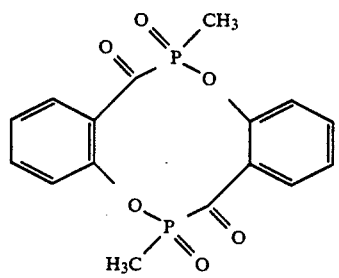

Name: 7,14-dioxo-6,13-dimethyl-dibenzo[d,i]-1,6-dioxa-2,7-diphosphecane 6,13-dioxide
Yield: 18 g (17 % of theory)
Melting point: 276° C.
NMR-data: $^{31}$P (CDCl$_3$) 43.9/44.2 ppm (2 isomers); $^1$H (80 MHz, CDCl$_3$) 1.66 ppm ($^1$J$_{P-C}$=17.9 Hz) (isomer 1) 1.75 ppm ($^1$J$_{P-C}$=17.6 Hz) (isomer 2) 7.2–8.1 ppm, multiplet
UV (acetonitrile): Maximum: 281 nm.

Example (6) Reaction of salicylic acid with methyldichlorophosphine

The reaction according to Example 5 is repeated using 232 g (1.7 mol) of salicylic acid and 197 g (1.7 mol) of methyldichlorophosphine in toluene (400 ml), 4-dimethylaminopyridine DMAP (5 g; 41 mmol) being added as catalyst. Violent formation of hydrogen chloride occurs mediately. The reaction is completed after 30 minutes.
Yield: 79.5 g (25.9 % of theory)
$^{31}$P-NMR (CDCl$_3$) 45.5/45.7 ppm.

Example (7) Reaction of 4-chlorosalicylic acid with phenyldichlorophosphine PhPCl$_2$ As in Example 1, 4-chlorosalicylic acid (81.3 g; 471 mmol) in toluene (170 ml) is reacted with phenyldichlorophosphine (84.3 g; 471 mmol) for 7 h at 110° C. Towards the end of the reaction, a fine solid is precipitated from the light-brown reaction mixture. The mixture is allowed to cool overnight, the solid is filtered off by suction and is washed twice using a small amount of toluene. Purification by further slurrying in toluene, filtering off by suction and drying in vacuo.

Formula:

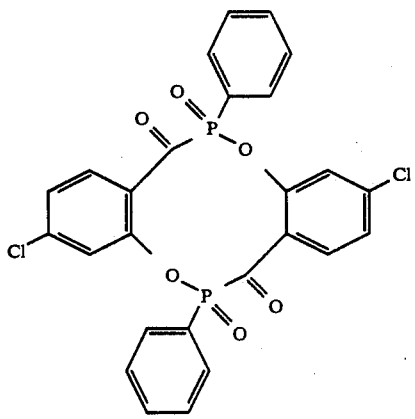

Name: 3,10-dichloro-7,14-dioxo-6,13-diphenyldibenzo-[d,i]-1,6-dioxa-2,7-diphosphecane 6,13-dioxide Yield: 77.4 g (59.0 % of theory)

Melting point: 243°-245° C.

NMR-data:

(CDCl$_3$): 31.5 ppm;

$^1$H (80 MHz, CDCl$_3$): 6.9-8.0 ppm (multiplet);

$^{13}$C (20.1 MHz, CDCl$_3$):

147.3 ppm; multiplet; C=O;

137.2 ppm; singlet; C-Cl;

135.9 ppm; multiplet; C-O;

134.1 ppm; singlet; C-H (benzo);

131.8 ppm; multiplet; C-H (P-phenyl);

129.0 ppm; multiplet; C-H (P-phenyl);

128.8 ppm; singlet; C-H (P-phenyl);

126.5 ppm; singlet: C-H (benzo); other peaks not assigned;

UV (acetonitrile): Maximum at 296 nm.

Example (8) Reaction of 5-chlorosalicylic acid with phenyldichlorophosphine

5-Chlorosalicylic acid (87.5 g; 507 mmol) in toluene (170 ml) is reacted, as in Example 1, with phenyldichlorophosphine (90.8 g; 507 mmol) for 7 h at 110° C. Towards the end of the reaction a fine solid precipitates out from the yellow reaction mixture. The mixture is allowed to cool overnight and the solid is filtered off using suction, washed several times with a small amount of toluene and dried in vacuo.

Formula:

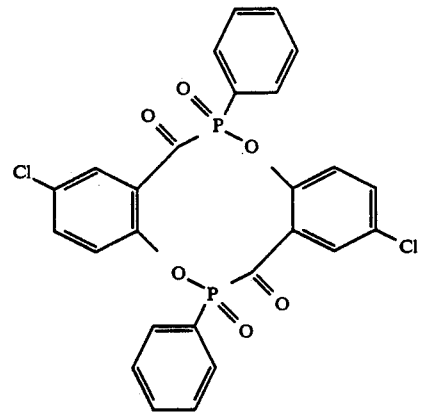

Name: 2,9-dichloro-7,14-dioxo-6,13-diphenyldibenzo-[d,i]-1,6-dioxa-2,7-diphosphecane 6,13-dioxide Yield: 112.2 g (79.4% of theory)

Melting point: 276°-278° C.

NMR-data: $^{31}$P (CDCl$_3$): 30.2 ppm;

UV (acetonitrile): Maximum at 281 nm.

Examples 9-14: See Tables 1 and 2

Example 15: Reaction of 3-hydroxy-2-naphthoic acid with phenyldichlorophosphine

3-Hydroxy-2-naphthoic acid (176 g; 935 mmol) in methyl glycol acetate (200 ml) is reacted with phenyldichlorophosphine (167.4 g; 935 mmol), as described in Example 1, initially for 5 h at 155° C. and then for 15 h at 100° C. A fine solid precipitates out, which is separated off and purified by repeated slurring in toluene and filtering. The drying is carried out in vacuo.

Formula:

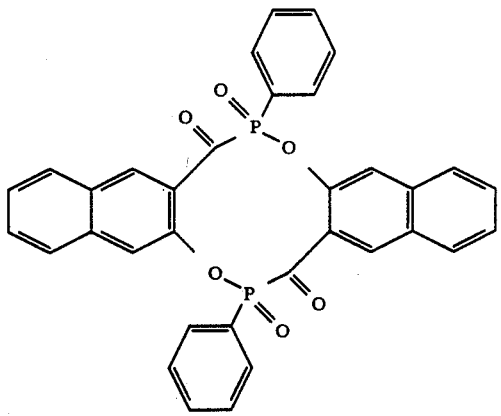

Name: 8,17-dioxo-7,16-diphenyldinaphtho[2,3-d:2',3,-i]-1,6-dioxa-2,7-diphosphecane 7,16-dioxide Yield: 146.2 g (54.1 % of theory)

Melting point: 280°-283° C.

$^{31}$P (81 MHz, CDCl$_3$): 28.0 ppm;

$^1$H (400 MHz, CDCl$_3$): 7.34-8.57 ppm (multiplet);

$^{13}$C (100 MHz, CDCl$_3$):

143.7 ppm; multiplet; C=O;

136.5 ppm; multiplet; C-O;

134.2 ppm; singlet; C (naphtho);

134.0 ppm; singlet; C-H (naphtho-);

132.1 ppm; multiplet; C-H (P-phenyl);

130.8 ppm; singlet; C (naphtho-);
129.4 ppm; singlet; C-H (naphtho);
128.9 ppm; multiplet; C-H (P-phenyl);
128.7 ppm; singlet; C-H (naphtho-);
128.2 ppm; singlet; C-H (P-phenyl);
127.4 ppm; singlet; C-H (naphtho-);
126.6 ppm; singlet; C-H (naphtho-);
124.8 ppm; doublet; $^1J(C\text{-}P)=188.3$ Hz; (P-phenyl)
123.4 ppm; singlet; C-CO;
119.1 ppm; singlet; CH-C-O;
MS (direct injection, 70 eV): m/e ($I_{rel}$, fragment)
588 (100, M+);
448 (17, M-PhPO$_2$+);
high resolution found (calculated): 588.0891 (588.089166)
UV (acetonitrile): Maxima at 324 and 270 nm.

Example 16: Reaction of 6-methoxy-3-hydroxy-2-naphthoic acid with phenyldichlorophosphine Analogously to Example 15, technical 3-hydroxy-6-methoxy-2-naphthoic acid (100 g; 458 mmol) in toluene (200 ml) is reacted for 8 hours at 110° C. with phenyldichlorophosphine (81.9 g; 458 mmol). A light-brown, still somewhat impure, crystalline product is isolated.

Formula:

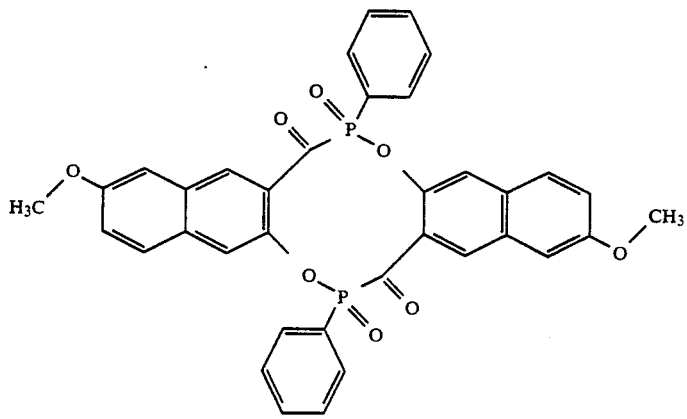

Name: 2,11-dimethoxy-8,17-dioxo-7,16-diphenyl-dinaphtho-[2,3-d:2',3,-i]-1,6-dioxa-2,7-diphosphecane 7,16-dioxide
Yield: 88 g (29.6 % of theory)
Melting point: >300° C.
NMR-data: $^{31}$P (CDCl$_3$): 30.6 ppm;
UV (acetonitrile): Maxima at 269 and 323 nm.

Example 17: Reaction of 3-hydroxy-2-naphthoic acid with methyldichlorophosphine 3-hydroxy-2-naphthoic acid (300 g; 1596 mmol) in toluene (300 ml) is reacted as described in Example 15 for 5 h at 110° C. with methyldichlorophosphine (185.1 g; 1596 mmol). A fine crystalline, colorless solid is obtained.

Formula:

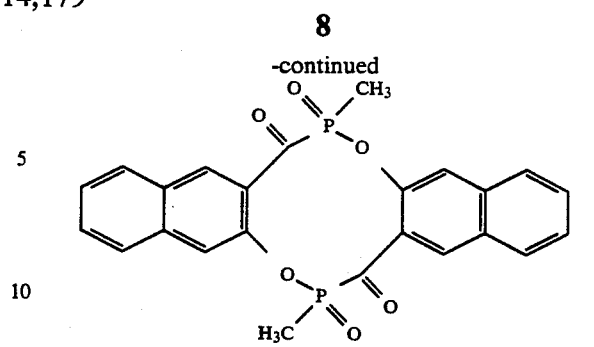

Name: 8,17-dioxo-7,16-dimethyldinaphtho[2,3-d:2,3,-i]-1,6-dioxa-2,7-diphosphecane 7,16-dioxide
Yield: 71.4 g (19.2 % of theory)
Melting point: 271°-280° C.
NMR-data: $^{31}$P (CDCl$_3$): 46.0 ppm;
UV (acetonitrile): Maxima at 269 and 322 nm

Example 18: Reaction of 3-hydroxy-2-naphthoic acid with s-butyldichlorophosphi===

3-Hydroxy-2-naphthoic acid (47.3 g; 252 mmol) in toluene (115 ml) is reacted as described in Example 15 for 6 h at 110° C. with s-butyldichlorophosphine (40.0 g; 252 mmol). A fine crystalline, colorless solid is obtained.

Formula:

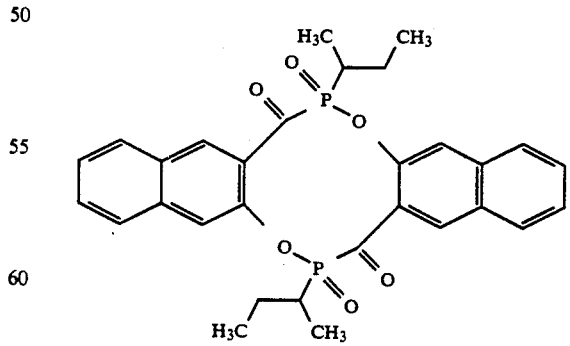

Name: 8,17-dioxo-7,16-bis(1-methylpropyl)dinaphtho[2,3-d:2'3'-i]-1,6-dioxa-2,7-diphosphecane 7,16-dioxide
Yield: 25.8 g (37.4% of theory)
Melting point: 238° C.

NMR-data: $^{31}$P (CDCl$_3$): 47.2–47.7 ppm (a plurality of isomers);

UV (acetonitrile): Maxima at 270 and 323 nm.

TABLE 1

Batch sizes and reaction conditions for Examples 9–14

| Example | Salicylic acid derivative | Amount [g (mmol)] | RPCl$_2$ | Amount [g (mmol)] | Solvent | Amount [ml] | Reaction temp. [°C.] | Reaction time [h] |
|---|---|---|---|---|---|---|---|---|
| 9 | 5-Bromosalicylic acid | 60 (276) | C$_6$H$_5$PCl$_2$ | 49.5 (276) | Toluene | 115 | 110 | 5 |
| 10 | 3,5-Dibromosalicylic acid | 60 (203) | C$_6$H$_5$PCl$_2$ | 36.3 (203) | Toluene | 115 | 110 | 3 |
| 11 | 5-Acetylsalicylic acid | 10.5 (58) | C$_6$H$_5$PCl$_2$ | 10.4 (58) | Toluene | 115 | 110 | 2.5 |
| 12 | 5-Nitrosalicylic acid | 12 (65) | C$_6$H$_5$PCl$_2$ | 15.5 (65) | Toluene | 115 | 110 | 2 |
| 13 | 3-Methylsalicylic acid | 100 (657) | C$_6$H$_5$PCl$_2$ | 117.4 (657) | Toluene | 115 | 110 | 6 |
| 14 | 3-Methoxysalicylic acid | 12 (71.3) | C$_6$H$_5$PCl$_2$ | 12.8 (71.6) | Toluene | 250 | 110 | 5 |

TABLE 2

Characterization of the products of Examples 9–14, Part 1

| Example | Formula | Name | Yield [g (%)] | Melting Point [°C.] | $^{31}$P-NMR [ppm] | UV-Maximum [nm] |
|---|---|---|---|---|---|---|
| 9 | [structure] | 2,9-dibromo-7,14-dioxo-6,13-diphenyldibenzo[d,i]-1,6-dioxa-2,7-diphosphecane 6,13-dioxide | 58.5 (65.1) | 196 | 31.3 (isomer 1) 30.9 (isomer 2) | 284 |
| 10 | [structure] | 2,4,9,11-tetrabromo-7,14-dioxo-6,13-diphenyldibenzo[d,i]-1,6-dioxa-2,7-diphosphecane 6,13-dioxide | 43.1 (53) | 288 >330 | 33.8 (isomer 1) 33.7 (isomer 2) | 290 |

TABLE 2-continued

Characterization of the products of Examples 9-14, Part 1

| Example | Formula | Name | Yield [g (%)] | Melting Point [°C.] | $^{31}$P-NMR [ppm] | UV-Maximum [nm] |
|---|---|---|---|---|---|---|
| 11 | | 2,9-diacetyl-7,14-dioxo-6,13-diphenyldibenzo[d,i]-1,6-dioxa-2,7-diphosphecane 6,13-dioxide | 10.3 (61.3) | 233–236 | 33.3 (isomer 1) 33.1 (isomer 2) | 286 |
| 12 | | 2,9-Dinitro-7,14-dioxo-6,13-diphenyl-dibenzo[d,i]-1,6-dioxa-2,7-diphosphecane 6,13-dioxide | 3.2 (15.0) | 264–266 | 33.2 (isomer 1) 31.3 (isomer 2) | 266 |
| 13 | | 4,11-Dimethyl-7,14-dioxo-6,13-diphenyl-dibenzo[d,i]-1,6-dioxa-2,7-diphosphecane 6,13-dioxide | 33.6 (19.8) | 207–218 | 30.8 (isomer 1) 30.7 (isomer 2) | 287 |

TABLE 2-continued
Characterization of the products of Examples 9-14, Part 1

| Example | Formula | Name | Yield [g (%)] | Melting Point [°C.] | $^{31}$P-NMR [ppm] | UV-Maximum [nm] |
|---|---|---|---|---|---|---|
| 14 | 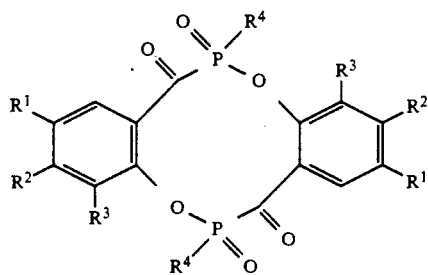 | 4,11-Dimethoxy-7,14-dioxo-6,13-diphenyl-dibenzo[d,i]-1,6-dioxa-2,7-diphosphecane 6,13-dioxide | 3.4 (17.4) | 210–215 | 31.9 | 286 |

We claim:

1. A cyclic acylphosphinic acid derivative of the formula

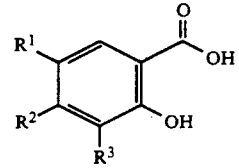

in which the substituents independently of each other have the following meaning:

$R^1$, $R^2$, $R^3$=H, halogen, C1- to C10-alkyl or -alkoxy phenyl, phenoxy, acetyl or $NO_2$, where $R^1$ and $R^2$ together with incorporation of the associated aromatic 6-ring, can also form an extended, unsubstituted or substituted aromatic ring system;

$R^4$=C1- to C4-alkyl, C5- or C6-cycloalkyl, phenyl or alkylphenyl.

2. The cyclic acylphosphinic acid derivative of the formula as claimed in claim 1, in which the substituents independently of each other have the following meaning: $R^1$, $R^2$, $R^3$=H, Cl, Br, $CH_3$, $CH_3O$, $CH_3CO$ or $NO_2$, where $R^1$ and $R^2$ together, with incorporation of the associated aromatic 6-ring, can also form a naphthalene structure, optionally substituted by a methoxy group;

$R^4$=methyl, sec-butyl or phenyl.

3. A process for the preparation of the cyclic acylphosphinic acid derivative as claimed in claim 1, which comprises reacting aromatic o-hydroxycarboxylic acids of the formula $$\begin{array}{c} R^1 \\ R^2 \end{array} \diagdown \bigcirc \diagup \begin{array}{c} C(=O)OH \\ OH \\ R^3 \end{array}$$

or their alkali metal salts with organyldichlorophosphines of the formula $R^4PCl_2$, where $R^1$, $R^2$, $R^3$ and $R^4$ have the meaning given, in an aprotic solvent or suspension medium at temperatures of 0° to 200° C., with elimination of gaseous hydrogen chloride or precipitation of alkali metal chloride and separating off, washing and drying the precipitated target product.

4. The process as claimed in claim 3, wherein the reaction is carried out in the presence of catalytic amounts of heterocyclic, aromatic compounds or quaternary ammonium or phosphonium salts.

* * * * *